United States Patent
Chen et al.

(10) Patent No.: US 10,450,358 B2
(45) Date of Patent: Oct. 22, 2019

(54) PLATELET-DERIVED GROWTH FACTOR B MUTANT, PREPARATION METHOD THEREFOR AND USE THEREOF

(71) Applicant: Institute of Biotechnology Academy of Military Medical Sciences P.L.A. China, Beijing (CN)

(72) Inventors: Wei Chen, Beijing (CN); Xiaopeng Zhang, Beijing (CN); Changming Yu, Beijing (CN); Ling Fu, Beijing (CN); Mengmeng Dai, Beijing (CN); Jun Zhang, Beijing (CN); Junjie Xu, Beijing (CN); Lihua Hou, Beijing (CN); Jianmin Li, Beijing (CN)

(73) Assignee: Institute of Biotechnology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/311,590

(22) PCT Filed: Jul. 16, 2015

(86) PCT No.: PCT/CN2015/084260
§ 371 (c)(1),
(2) Date: Nov. 16, 2016

(87) PCT Pub. No.: WO2015/172752
PCT Pub. Date: Nov. 19, 2015

(65) Prior Publication Data
US 2017/0253642 A1 Sep. 7, 2017

(30) Foreign Application Priority Data
May 16, 2014 (CN) .......................... 2014 1 0206900

(51) Int. Cl.
| | | |
|---|---|---|
| C07K 14/49 | (2006.01) |
| A61K 38/18 | (2006.01) |
| C07K 1/16 | (2006.01) |
| C07K 1/18 | (2006.01) |
| C07K 1/20 | (2006.01) |
| C07K 16/22 | (2006.01) |
| C07K 19/00 | (2006.01) |
| C12N 5/10 | (2006.01) |
| C12N 15/63 | (2006.01) |
| B01D 15/20 | (2006.01) |
| B01D 15/32 | (2006.01) |
| B01D 15/34 | (2006.01) |
| B01D 15/36 | (2006.01) |
| B01D 15/42 | (2006.01) |
| A61K 38/00 | (2006.01) |

(52) U.S. Cl.
CPC .............. *C07K 14/49* (2013.01); *A61K 38/18* (2013.01); *B01D 15/203* (2013.01); *B01D 15/327* (2013.01); *B01D 15/34* (2013.01); *B01D 15/361* (2013.01); *B01D 15/426* (2013.01); *C07K 1/16* (2013.01); *C07K 1/18* (2013.01); *C07K 1/20* (2013.01); *C07K 16/22* (2013.01); *C07K 19/00* (2013.01); *C12N 5/10* (2013.01); *C12N 15/63* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,149,792 A | 9/1992 | Thomason | |
| 5,512,545 A * | 4/1996 | Brown | C07K 14/49 435/252.33 |
| 5,516,896 A * | 5/1996 | Murray | A61K 35/16 435/252.3 |
| 5,905,142 A * | 5/1999 | Murray | C07K 14/49 530/350 |
| 6,194,169 B1 * | 2/2001 | Kaetzel | C07K 14/49 435/252.3 |
| 8,114,841 B2 * | 2/2012 | Lynch | A61L 27/12 424/484 |
| 8,772,236 B2 * | 7/2014 | Timmerman | C07K 14/52 514/1.1 |
| 2003/0046716 A1 * | 3/2003 | Echelard | C07K 14/49 800/7 |

FOREIGN PATENT DOCUMENTS

| | | |
|---|---|---|
| CN | 1082921 A | 3/1994 |
| CN | 1508259 A | 6/2004 |
| CN | 1661011 A | 8/2005 |
| JP | H04334399 | 11/1992 |
| JP | 2001-518073 | 10/2001 |

(Continued)

OTHER PUBLICATIONS

Setterini et al., Biomedical and Environmental Mass Spectrometry, vol. 19, pp. 665-676, 1990.*

(Continued)

*Primary Examiner* — Marianne P Allen
(74) *Attorney, Agent, or Firm* — Sterne, Kessler, Goldstein & Fox P.L.L.C.

(57) ABSTRACT

Provided are a platelet-derived growth factor B derivative, the encoding nucleic acid molecule thereof, and a vector and host cell having the nucleic acid molecule. Also provided are a preparation method for the mutant, and the use of the mutant in preparing medications for promoting cell division, cell proliferation, wound healing, skin regeneration, bone and tooth defect regeneration, and joint repair.

Figure 1:
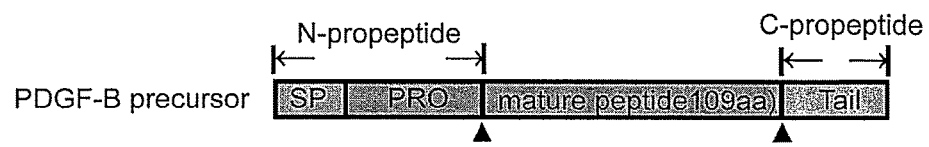
Figure 1:
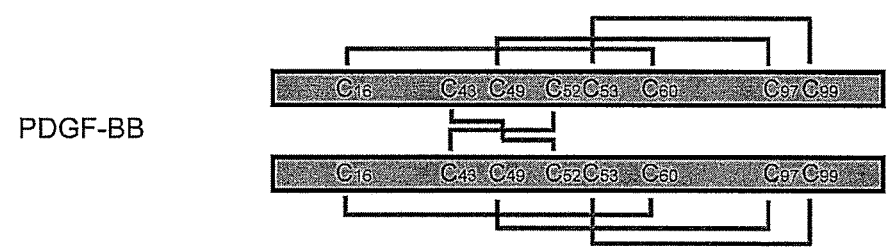

11 Claims, 6 Drawing Sheets
Specification includes a Sequence Listing.

(56) References Cited

FOREIGN PATENT DOCUMENTS

| WO | WO 91/16335 | * | 10/1991 |
|---|---|---|---|
| WO | WO 92/01716 A1 | | 2/1992 |
| WO | WO 2014/072876 | | 5/2014 |

OTHER PUBLICATIONS

International Search Report (ISR) for PCT/CN2015/084260; I.A. fd: Jul. 16, 2015, dated Oct. 21, 2015, State Intellectual Property Office of the P.R. China, Beijing, China.

International Preliminary Report on Patentability (IPRP) including the Written Opinion of the International Searching Authority (PCT Rule 44bis) for PCT/CN2015/084260; I.A. fd: Jul. 16, 2015, dated Nov. 22, 2016, by the International Bureau of WIPO, Geneva, Switzerland.

Oefner, C. et al., "Crystal structure of human platelet-derived growth factor BB," EMBO J (Nov. 1992);11(11):3921-3926, IRL Press, Oxford, England.

Chen, J et al., "Molecular cloning and expression of human PDGF-B chain mature peptide gene," Zhonghua wai ke za zhi [Chinese journal of surgery].42:1170-1173 (Oct. 2004), Zhonghua yi xue hui, Wai ke xue hui publisher, Beijing, China.

Office action for Japanese Patent Application No. 2017-512094, dated Jul. 31, 2018, The Japanese Patent Office, Tokyo, Japan.

Office action for Korean Patent Application No. 10-2016-7035429, dated Aug. 9, 2018, The Korean Intellectual Property Office, Daejeon, Republic of Korea.

Office action and search report for Chinese Patent Application No. 201410206900.1, dated Nov. 29, 2017, Chinese Patent Office, Beijing City, China.

Office action for Chinese Patent Application No. 201410206900.1, dated Jul. 2, 2018, Chinese Patent Office, Beijing City, China.

Kaetzel Jr. et al., "Site-directed mutagenesis of the N-linked glycosylation site in platelet-derived growth factor B-chain results in diminished intracellular retention," *Biochim. Biophys. Acta*, 1289:250-260, Elsevier Science B.V., (Dec. 5, 1996).

Extended European Search Report for European Application No. 15793254.2, European Patent Office, Munich Germany, dated Aug. 3, 2018.

Clements et al., "Two PDGF-B chain residues, arginine 27 and isoleucine 30, mediate receptor binding and activation," *The EMBO Journal*, 10:4113-4120, Oxford University Press, (1991).

Office action for Chinese Patent Application No. 201410206900.1, dated Jan. 4, 2019, Chinese Patent Office, Beijing City, China.

Office action for Korean Patent Application No. 10-2016-7035429, dated Feb. 28, 2019, The Korean Intellectual Property Office, Daejeon, Republic of Korea.

* cited by examiner

A

B

PLATELET-DERIVED GROWTH FACTOR B MUTANT, PREPARATION METHOD THEREFOR AND USE THEREOF

REFERENCE TO SEQUENCE LISTING SUBMITTED ELECTRONICALLY

The content of the electronically submitted substitute sequence listing, file name 3932_0010001_SeqListing.txt, size 7247 bytes; and date of creation Dec. 31, 2016, filed herewith, is incorporated herein by reference in its entirety.

TECHNICAL FIELD

The present invention relates to a platelet-derived growth factor B derivative. Specifically, the present invention relates to a platelet-derived growth factor B mutant, a nucleic acid molecule encoding the mutant, a vector and a host cell containing the nucleic acid molecule. The present invention also relates to a method for preparing and purifying said mutant, and to a use of said mutant for preparation of a medicament for promoting cell division and proliferation, promoting wound healing, skin regeneration, bone and damaged tooth regeneration and joint repair.

BACKGROUND ART

Platelet-derived growth factor (PDGF) is a polypeptide that can be produced by diverse cells and can stimulate the proliferation of stroma-derived cells. In the 1970s, it was first discovered by Ross et. al. from the platelet, and thus named (1). So far, a total of four PDGF monomers, namely, PDGF-A, PDGF-B, PDGF-C and PDGF-D, have been found. These monomers form five kinds of homo-or heterodimers with each other via intrachain and interchain disulfide bonds: PDGF-AA, PDGF-BB, PDGF-AB, PDGF-CC, and PDGF-DD (2, 3). It is generally accepted that PDGF genes and proteins belong to a family of structurally and functionally related growth factors, which also includes vascular endothelial growth factor (VEGFs) and placental growth factor (PIGF) (4). PDGF plays a physiological role by activating its receptor PDGF-Rs. PDGF-Rs include both PDGFR-α and PDGFR-β, belonging to tyrosine kinase receptor. Binding of a ligand to a receptor triggers the dimerization of receptor monomers, leading to the autophosphorylation and activation of intracellular tyrosine residues. Both receptors can activate the critical molecules in multiple signaling pathways, such as Ras-MAPK, PI3K and PLC-γ (5), in turn activate transcription of the related genes, stimulate cell growth, inhibit apoptosis, promote differentiation and induce oriented movement, migration, and the like, and play a variety of biological functions.

PDGF-b gene is located on chromosome 22 and contains seven exons. It encodes a precursor protein consisting of 241 amino acids and its final mature product formed by proteolytic processing is a polypeptide consisting of 109 amino acids, with a molecular weight of 12.3 kD. In organisms, the active form of PDGF-B protein is homodimer PDGF-BB or heterodimer PDGF-AB formed from two monomers via disulfide bonds (6). Each PDGF-B protein monomer contains eight highly conserved cysteine residues, wherein six cysteines form intrachain disulfide bonds (Cys I-VI, III-VII, V-VIII), and the other two form interchain disulfide bonds with the corresponding monomers (Cys II-IV) (7), together forming the growth factor domains-characteristic of the PDGF protein family, i.e., cystine knots. These intra-and inter-chain disulfide bonds constitute a complex spatial structure of the PDGF-BB dimer protein (FIG. 1B).

In addition, different splicing forms of PDGF protein exist during the expression and synthesis of the protein, so that the PDGF protein upon processing and maturation exhibits a variety of structural forms. N-terminal amino acid sequence analysis of the PDGF-BB isolated and purified from human platelet extracts indicates the presence of at least three different splicing forms, 20% Ser1, 45% Thr6 and 35% Thr33. The heterogeneity of these cleavage products renders the proportion of proteins in various cleavage forms uncontrollable when purifying PDGF-BB (8).

SUMMARY OF THE INVENTION

The inventors of the present invention have made extensive studies and found that the site-specific protease degradation and/or glycosylation modification is the main reason responsible for the presence of various PDGF-Bs, and in turn, obtained PDGF-B mutants by site mutation. The mutant has a greatly enhanced homogeneity and still retains the activity of PDGF-B protein.

The first aspect of the present invention relates to a platelet-derived growth factor B mutant having mutations at amino acid positions 101 and 109 of wild-type platelet-derived growth factor B (the descriptions of amino acid site positions herein are all based on the mature PDGF-B comprising 109 amino acid residues, the same hereinafter), and having the activity of platelet-derived growth factor B.

The platelet-derived growth factor B mutant according to any one of the first aspect of the present invention has a mutation at the amino acid position 6 and has the activity of platelet-derived growth factor B.

The platelet-derived growth factor B mutant according to any one of the first aspect of the present invention has mutation(s) at the amino acid positions 32 and/or 33 and has the activity of platelet-derived growth factor B.

The platelet-derived growth factor B mutant according to any one of the first aspect of the present invention has an N-terminal deletion of 5 amino acids compared with wild-type platelet-derived growth factor B and has the activity of platelet-derived growth factor B.

In one embodiment of the invention, the mutant has mutations to alanine at the amino acid positions 6, 101 and 109.

In another embodiment of the invention, the mutant has mutations to alanine at the amino acid positions 101 and 109.

The platelet-derived growth factor B mutant according to any one of the first aspect of the present invention has mutation(s) to proline, valine or isoleucine at the amino acid positions 32 and/or 33.

In one embodiment of the invention, the mutant has a mutation to proline, valine or isoleucine, preferably proline, at the amino acid position 32.

The platelet-derived growth factor B mutant according to any one of the first aspect of the present invention, wherein said platelet-derived growth factor B is a mammalian derived platelet-derived growth factor B, and the mammal is, for example, a human or a mouse.

In one embodiment of the invention, the platelet-derived growth factor B mutant has an N-terminal deletion of 5 amino acids, mutations to alanine at the amino acid positions 6, 101 and 109, and a mutation to proline at the amino acid position 32.

In one embodiment of the invention, the platelet-derived growth factor B mutant has an N-terminal deletion of 5 amino acids, mutations to alanine at the amino acid positions 101 and 109, and a mutation to proline at the amino acid position 32.

In one embodiment of the invention, the platelet-derived growth factor B mutant has an N-terminal deletion of 5 amino acids, mutations to alanine at the amino acid positions 6, 101 and 109, and a mutation to valine at the amino acid position 32.

In one embodiment of the invention, the platelet-derived growth factor B mutant has an N-terminal deletion of 5 amino acids, mutations to alanine at the amino acid positions 6, 101 and 109, and a mutation to isoleucine at the amino acid position 32.

The present invention also encompasses the combinations of the above-described various technical solutions.

In specific embodiments of the invention, the amino acid sequence of the mutant is the sequence set forth in SEQ ID NO: 3 or SEQ ID NO: 5.

The platelet-derived growth factor B mutant according to any one of the first aspect of the present invention has substitution(s), deletion(s) or addition(s) of one or more amino acids in its amino acid sequence and has the activity of platelet-derived growth factor B.

It is well known to those skilled in the art that substitution(s), deletion(s) or addition(s) of one or more amino acids at the non-essential positions of a protein can be made without affecting the activity of the protein. In the present invention, the mutants resulting from substitution(s), deletion(s) and/or addition(s) of one or more amino acids at the non-essential positions other than the amino acid mutation positions mentioned above and still retaining the activity of platelet-derived growth factor B are also within the protection scope of the present invention.

The second aspect of the present invention relates to a platelet-derived growth factor homodimer or heterodimer formed by two platelet-derived growth factor B mutants according to any one of the first aspect of the present invention via intra-and/or inter-chain disulfide bonding, or formed by one platelet-derived growth factor B mutant according to any one of the first aspect of the present invention and one platelet-derived growth factor A via intra-and/or inter-chain disulfide bonding.

In the present invention, the platelet-derived growth factor homodimer or heterodimer is formed in the same manner as the wild-type platelet-derived growth factor.

In embodiments of the invention, the two platelet-derived growth factor B mutants of any one of the first aspect of the present invention are bound via intra-and inter-chain disulfide bonds to form a PDGF-BB mutant.

A third aspect of the present invention relates to a nucleic acid molecule encoding the platelet-derived growth factor B mutant of any one of the first aspect of the present invention.

The nucleic acid molecule according to any one of the third aspect of the invention has a nucleotide sequence selected from the group consisting of sequences SEQ ID NO: 4, SEQ ID NOs: 6-9.

A fourth aspect of the present invention relates to a vector comprising the nucleic acid molecule according to any one of the third aspect of the invention.

In the present invention, the expression vector can be selected by those skilled in the art depending on the host cell used for expression, for example, a vector suitable for expression in a yeast cell or a mammalian cell can be selected.

In an embodiments of the invention, the vector is pMEX9K.

A fifth aspect of the present invention relates to a host cell comprising the vector of any one of the fourth aspect of the invention.

The host cell according to any one of the fifth aspect of the invention is a eukaryotic cell, for example, a yeast cell, a mammalian cell or an insect cell.

The host cell according to any one of the fifth aspect of the invention is a yeast cell, for example, *Pichia pastoris, Saccharomyces cerevisiae, Kluyveromyces lactis, Hansenula, Candida* or *Torulopsis*.

In embodiments of the invention, the *Pichia pastoris* cell strain is GS115.

The host cell according to any one of the fifth aspect of the present invention is a mammalian cell, for example, a CHO cell, a BHK cell, an NS0 cell, an SP2/0 cell, an HEK-293 cell, a COS cell and the like.

The present invention also relates to a method for preparation of the platelet-derived growth factor B mutant of any one of the first aspect of the invention, comprising the steps of subjecting the host cell of any one of the fifth aspect of the invention to culture, expression (e.g., induced expression) and optionally purification.

The preparation method according to the present invention, comprising the steps of:

1) inoculating the host cells of any one of the fifth aspect of the present invention into a culture medium, followed by stepwise culture and propagation;

2) collecting the host cells, resuspending the recombinant cells into the medium, and adding methanol to induce expression;

3) after the completion of the induction expression, collecting and purifying the culture supernatant to obtain the platelet-derived growth factor B protein.

The preparation method according to any one of the present invention, characterized in one or more of the following:

(1) the host cell in step 1) is a monoclonal cell line;

(2) the stepwise culture and propagation described in step 1) refers to two-stage culture and propagation, the culture temperature is 28-30° C., and the cell is cultured in each stage to an $OD_{600}$ of 1-12, for example 2-6;

(3) the temperature for inducing expression in step 2) is about 28° C.;

(4) the final concentration of methanol in step (2) is 0.3-1.0% (v/v), for example 0.4-0.8% (v/v), for example 0.5% (v/v);

(5) the time for inducing expression in step 2) is 48-96 h, for example 72 h;

(6) the purification step in step 3) successively comprises hydrophobic interaction chromatography, ion exchange chromatography, and gel filtration chromatography.

A sixth aspect of the present invention relates to a method for purifying platelet-derived growth factor B or a mutant thereof, comprising the steps of successively subjecting a culture supernatant or a cell lysate containing platelet-derived growth factor B or a mutant thereof to hydrophobic interaction chromatography, ion exchange chromatography and gel filtration chromatography.

The purification method according to any one of the sixth aspect of the present invention, wherein the platelet-derived growth factor B mutant is the platelet-derived growth factor B mutant of any one of the first aspect of the present invention.

In embodiments of the present invention, the chromatographic column medium used for hydrophobic interaction chromatography is Phenyl Sepharose 6 Fast Flow.

In embodiments of the present invention, the chromatography medium used for the ion exchange chromatography is Source 30S.

In embodiments of the present invention, the chromatography medium used for gel filtration chromatography is Hiload Superdex 75 prep grad.

The purification method according to any one of the sixth aspect of the present invention, wherein:

said hydrophobic interaction chromatography comprises the steps of:

(1) adjusting the conductivity of the culture supernatant or cell lysate containing platelet-derived growth factor B or a mutant thereof with a conditioning buffer, and the final system with said conditioning buffer added is 10-50 mM phosphate buffer, 0.8-1M $(NH_4)_2SO_4$, pH 6.8-7.5;

(2) equilibrating the column with an equilibration buffer, and the formulation of the equilibration buffer is 10-50 mM phosphate buffer, 0.8-1M $(NH_4)_2SO_4$, pH 6.8-7.5;

(3) after loading the sample onto the column, washing the column with the equilibration buffer;

(4) eluting with an elution buffer and collecting the protein of interest, and the formulation of the elution buffer is 10-50 mM phosphate buffer, 30%-50% ethylene glycol, pH 6.8-7.5; said ion exchange chromatography comprises the steps of:

(1) diluting the elution peak of hydrophobic interaction chromatography with an equilibration buffer to a conductivity of 6 mS/cm or less, and the formulation of the equilibration buffer is 10-50 mM phosphate buffer, pH 6.8-7.5;

(2) equilibrating the column with the equilibration buffer;

(3) after loading the sample onto the column, washing the column with the equilibration buffer;

(4) gradient eluting with an elution buffer and collecting the protein of interest, and the formulation of the elution buffer is 10-50 mM phosphate buffer, 0.8-1.2M NaCl, pH 6.8-7.5;

said gel filtration chromatography comprises the steps of:

(1) equilibrating the column with a phosphate buffer, and the formulation of the phosphate buffer is 10-50 mM phosphate buffer, 0.1-0.5M NaCl, pH 6.8-7.5;

(2) loading the elution peak of the ion exchange chromatography, and the volume of each loading is not more than 0.3 to 4% (for example, 3%) of the column volume;

(3) continuing to wash the column with the phosphate buffer in step (1), collecting the protein of interest, and obtaining the purified platelet-derived growth factor B or the mutant thereof. In the present invention, the formulation of the phosphate buffer is well known in the art. In embodiments of the present invention, the phosphate buffer is 20 mM PB solution containing 0.0144 mol/L $Na_2HPO_4$ and 0.0056 mol/L $NaH_2PO_4$, pH 6.8-7.5.

In the present invention, the formulation of the phosphate buffer is well known in the art. In embodiments of the present invention, the phosphate buffer is PBS solution and the formulation thereof is 10-50 mM PB solution, 0.15M NaCl, pH 6.8-7.5.

In embodiments of the invention, the pH value of the buffer for each step of chromatography is 7.2.

In embodiments of the invention, the concentration of the phosphate buffer for each step of chromatography is 20 mM.

In a specific embodiment of the present invention, the hydrophobic interaction chromatography is carried out as follows. (1) Yeast expression supernatant is adjusted for conductivity with ½ volume of a conditioning buffer (60 mM PB, 3M $(NH_4)_2SO_4$, pH 7.2). (2) The column is equilibrated with equilibration buffer (20 mM PB, 1M $(NH_4)_2SO_4$, pH 7.2). (3) The sample is loaded to the column, thereafter the column is washed with the equilibration buffer until the baseline is flat. (4) The column is eluted with an elution buffer (20 mM PB, 50% ethylene glycol, pH 7.2) to collect the protein of interest.

In a specific embodiment of the present invention, the ion exchange chromatography is carried out as follows. (1) The Phenyl HS elution peak is diluted with an equilibration buffer (20 mM PB, pH 7.2) to a conductivity of 6 mS/cm or less. (2)The column is equilibrated with the equilibration buffer. (3) The sample is loaded to the column, thereafter the column is washed with the equilibration buffer until the baseline is flat. (4) The column is eluted with a gradient of elution buffer (20 mM PB, 1M NaCl, pH 7.2) to collect the protein of interest.

In a specific embodiment of the present invention, the gel filtration chromatography is carried out as follows. (1) The column is equilibrated with PBS buffer (20 mM PB, 0.15M NaCl, pH 7.2); (2) The Source 30S elution peak is loaded with a loop, and the volume of each loading is not more than 3% of the column volume. (3) The column is washed with PBS buffer to collect the protein of interest.

The present invention further relates to a use of the platelet-derived growth factor B mutant according to any one of the first aspect of the present invention for preparation of a medicament for promoting cell division, proliferation, promoting wound healing, skin regeneration, bone and damaged tooth regeneration, joint repair.

The present invention further relates to a method for promoting cell division, proliferation, promoting wound healing, skin regeneration, bone and damaged tooth regeneration, joint repair, comprising the step of administering to a subject in need thereof an effective amount of the platelet-derived growth factor B mutant of any one of the first aspect of the invention.

The present invention further relates to an antibody capable of specifically binding to the platelet-derived growth factor B mutant of any one of the first aspect of the invention.

The present invention also relates to a method for homogenizing the expression of a platelet-derived growth factor, comprising the step of engineering the amino acid sequence of the wild-type platelet-derived growth factor, the engineering comprising one or more of the following a) to c):

a) mutations at amino acid positions 101 and 109;
b) a mutation at amino acid position 6;
c) mutation(s) at amino acid positions 32 and/or 33;
d) N-terminal deletion of 5 amino acids.

The method according to any one of the present invention, characterized in one or more of the following i)-iii):

i) mutating the amino acids at positions 101 and 109 to alanine;
ii) mutating the amino acid at position 6 to alanine;
iii) mutating the amino acid(s) at positions 32 and/or 33 to proline, valine, or isoleucine.

The method according to any one of the present invention uses an eukaryotic expression system for expression, such as yeast cell expression system and mammalian cell expression system.

In one embodiment of the invention, the engineering refers to an N-terminal deletion of 5 amino acids, mutations to alanine at the amino acid positions 6, 101 and 109, and a mutation to proline at the amino acid position 32.

In one embodiment of the invention, the engineering refers to an N-terminal deletion of 5 amino acids, mutations to alanine at the amino acid positions 101 and 109, and a mutation to proline at the amino acid position 32.

In one embodiment of the invention, the engineering refers to an N-terminal deletion of 5 amino acids, mutations to alanine at the amino acid positions 6, 101 and 109, and a mutation to valine at the amino acid position 32.

In one embodiment of the invention, the engineering refers to an N-terminal deletion of 5 amino acids, mutations to alanine at the amino acid positions 6, 101 and 109, and a mutation to isoleucine at the amino acid position 32.

In specific embodiments of the invention, the amino acid sequence of the engineered platelet-derived growth factor is the sequence set forth in SEQ ID NO: 3 or SEQ ID NO: 5.

The present invention also encompasses the combinations of the above-described various technical solutions.

In the present invention, the vector is, for example, a cloning vector or an expression vector. The vector contains the nucleic acid molecule according to the present invention, and the vector can be obtained, for example, by inserting the above-described nucleic acid molecule into a cloning vector or an expression vector, or can be obtained by artificial synthesis.

Said expression vector is, for example, a prokaryotic expression vector, a eukaryotic expression vector, a phage vector or a viral vector. The prokaryotic expression vector is, for example, pET vector, or pGEX vector. The eukaryotic expression vector is, for example, pcDNA3.1, pEGFP-C1, pPIC9K, pMEX9K, pPICZ, pPICZa, pFastBac, pPIC6aA, pPIC3.5K, pGAPZaA, or pAO815. The phage vector is, for example, λ phage vector λgt, or λgt-λB. The virus vector is, for example, retrovirus, lentivirus, adenovirus or adeno-associated virus vector. In an embodiment of the invention, the vector is pMEX9K.

In the present invention, the host cell may be a prokaryotic cell (e.g., *E. coli* cell) or a eukaryotic cell. The eukaryotic cell is, for example, a yeast cell, a mammalian cell, or an insect cell. The host cell can be obtained by introducing/transfecting the nucleotide sequence of the above-described nucleic acid molecule or the vector into prokaryotic cells or eukaryotic cells.

In the present invention, the yeast cell lines are well known in the art and include, but are not limited to, X33, KM71, KM71H, GS115, SMD1168, SMD1163, SMD1168H, and SMD1163H.

In the present invention, the host cells transfected with a specific nucleic acid or vector can be obtained using any kind of transfection methods known in the art. For example, the nucleic acid can be introduced into the cells by electroporation or microinjection; or alternatively, lipofectin agents such as FuGENE 6, X-tremeGENE and LipofectAmine can be used; or alternatively, the nucleic acid can be introduced into cells by appropriate viral vectors based on a retrovirus, a lentivirus, an adenovirus or an adeno-associated virus.

In the present invention, the expression homogeneity means that, when the loading amount for electrophoresis is not less than 10 μg, reducing SDS-PAGE electrophoresis analysis demonstrates that the protein of interest is a single band as shown by Coomassie Brilliant Blue staining, and the software such as Image J or Bandscan indicates a purity >95%. Those skilled in the art may achieve more homogenous expression of the protein by trying and employing various techniques for different proteins.

In the present invention, a wild-type platelet-derived growth factor B refers to a non-mutated platelet-derived growth factor B having a length of 109 amino acids; and the descriptions of each site (e.g., mutation site, glycosylation site, cleavage site) are also based on the wild-type platelet-derived growth factor B as a reference.

In the present invention, the amino acids at positions 6, 101 and 109 of the wild-type platelet-derived growth factor B are all threonine (Thr); the amino acids at position 32 and 33 of the wild-type platelet-derived growth factor B are arginine (Arg); and the first five amino acids at N-terminus of the wild-type platelet-derived growth factor B are serine (Ser), leucine (Leu), glycine (Gly), serine (Ser), and leucine (Leu).

In the present invention, the term "about" means being within the range of 90% to 110%, for example, 95% to 105% of a value.

In the present invention, the PDGF-B mutant is obtained by mutation, its protein homogeneity is significantly improved, and the mutant retains the activity of PDGF-B protein.

DESCRIPTION OF THE DRAWINGS

FIG. 1. The schematic diagram of the structure of PDGF-B protein. A. PDGF-B precursor protein was removed of N-terminal signal peptide, propeptide and C-terminal propeptide sequence by proteolysis to become a mature protein. ▲ represents protease hydrolysis sites; B, two PDGF-B monomers form a PDGF-BB homodimer via interchain disulfide bonds, and each PDGF-B monomer contains eight cysteines, forming three pairs of intrachain disulfide bonds (C16-C60, C49-C97, C53-C99) and two pairs of interchain disulfide bonds (C43-052, C52-C43). SP: signal peptide; PRO: the pro-sequence preceding the growth factor domain.

FIG. 2. SDS-PAGE electrophoresis analysis of PDGF-BB expressed and secreted by *Pichia pastoris*. Non-reducing (left) and reducing (right) SDS-PAGE analysis were performed on three different batches of fermented and purified recombinant PDGF-BB$^{Thr6}$. Under the non-reducing condition, the protein is a single band. Upon DTT treatment, the PDGF-B monomers exhibit various forms with heterogeneous molecular weights.

FIG. 3. The co-effect of the proteolysis and glycosylation contributes to the formation of several monomers of PDGF-B$^{Thr6}$. (A) PDGF-B$^{Thr6}$ protein was separated by SDS-PAGE under reducing condition for N-terminal amino acid sequence analysis. The first five amino acid residues at N-terminus in the first, second and third bands are all TIATP, and the first five amino acid residues at N-terminus in the fourth and fifth bands are TNANF, suggesting that protease cleavage occurs at Arg32-Thr33. (B) PDGF-B$^{Thr6}$ protein was subjected to WB (middle) and glycoprotein staining (right) analysis under reducing conditions. WB detection bands correspond to bands 3 and 5 of Coomassie Brilliant Blue staining (left), and the glycoprotein staining bands correspond to bands 1, 2 and 4 of Coomassie Brilliant Blue staining. (C) PDGF-B$^{Thr6}$ protein was treated with PNGase F under reducing condition and stained for glycoprotein. There was no change in terms of band type, molecule weight (left) and glycoprotein staining results before and after treatment with PNGase F. IFN-ω serves as positive control for glycosidase cleavage and glycoprotein staining.

FIG. 4. Prediction results of O-linked glycosylation sites of PDGF-B$^{Thr6}$ protein sequence. Thr6, Thr101 and Thr109 are potential O-linked glycosylation modification sites.

FIG. 5. Purity of the purified protein PDGF-M2 upon HPLC detection.

FIG. 6. Analysis of post-translational modification sites of PDGF-B expressed in *Pichia pastoris*. (A) The schematic diagram of site mutation of PDGF-M1 and PDGF-M2 mutants. (B) WB detection showed PDGF-M1 and PDGF- M2 monomers as single bands, and control PDGF-BThr6 as two bands. (C) The PDGF-M1 and PDGF-M2 monomers were detected by SDS-PAGE, Coomassie Brilliant Blue staining result showed PDGF-M2 as a single protein band and PDGF-M1 as two protein bands (as shown by the arrows in the figure). (D) Glycoprotein staining can hardly detect PDGF-M1 and PDGF-M2 protein monomers.

Figure 7:
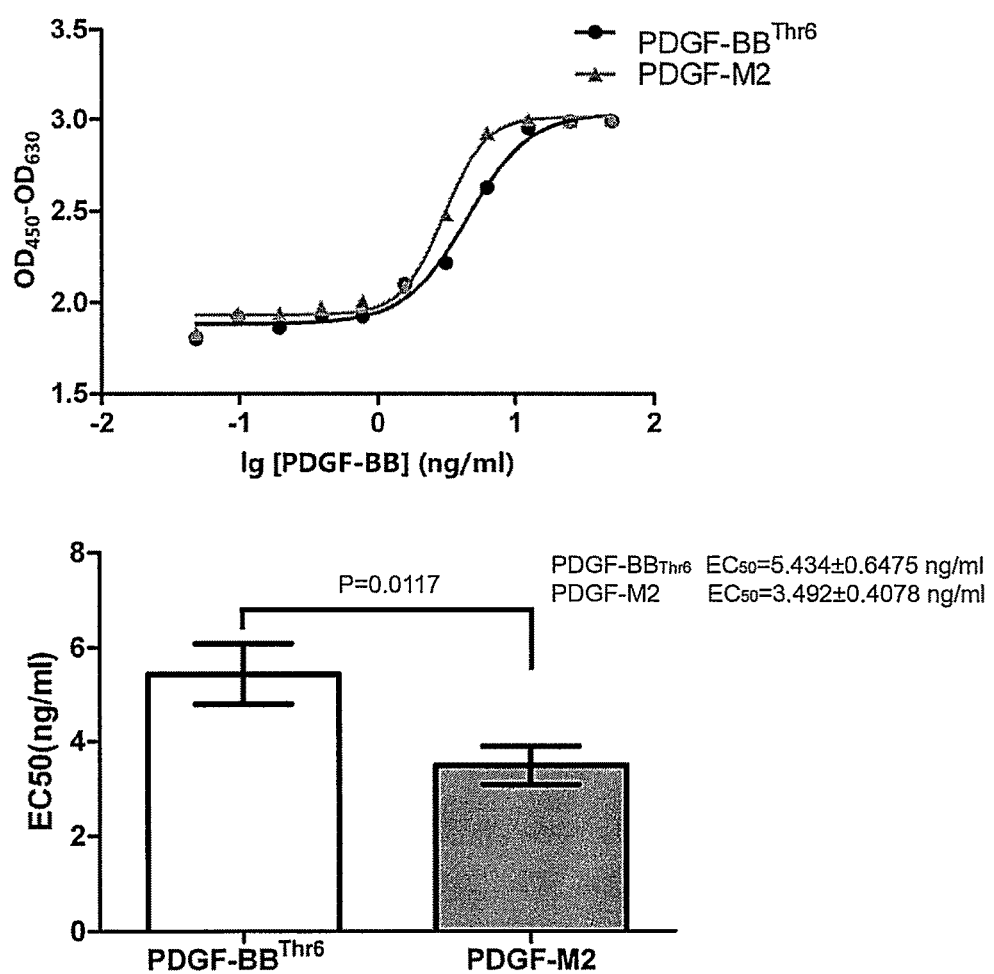

FIG. 7. The biological activity of PDGF-M2 is higher than that of PDGF-BB$^{Thr6}$, and there is statistically significant difference between them. The experiment was repeated three times, with EC50 expressed as mean ± standard deviation, P=0.039.

Figure 8:
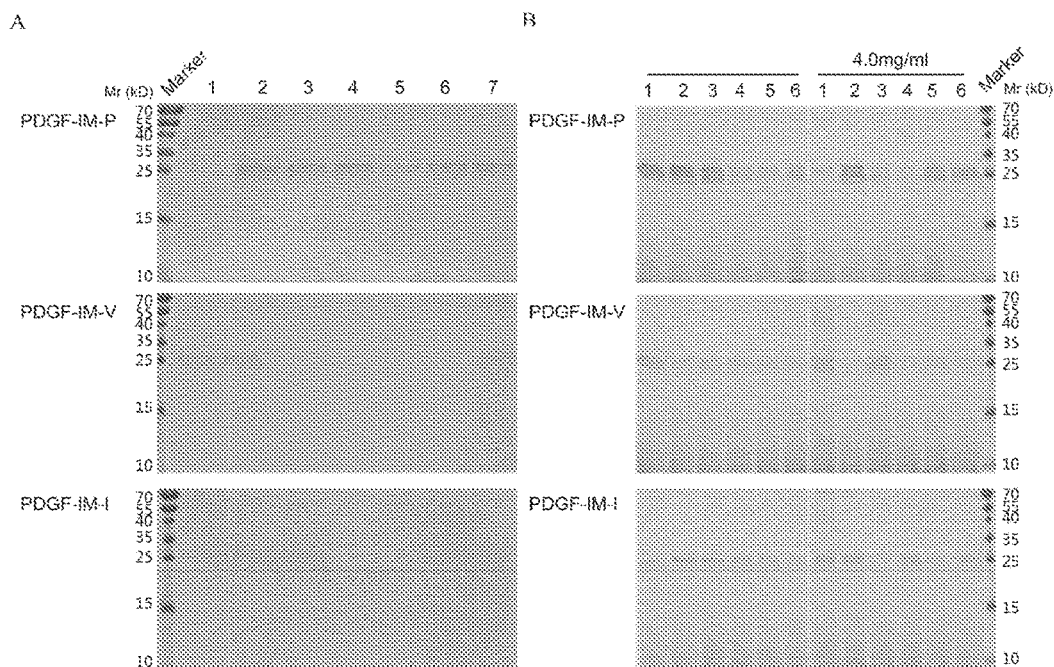

FIG. 8. The effect of mutation of Arg32 on the expression. (A) The SDS-PAGE results of the expression products of 7 clones of each of codon-optimized strains PDGF-IM-P, PDGF-IM-V and PDGF-IM-I. The protein expression amount of PDGF-IM-P is significantly higher than the other two strains. (B) The codon-optimized strains PDGF-IM-P, PDGF-IM-V and PDGF-IM-I were screened for multiple insert copies by G418 resistance, respectively. Six clones were selected under the G418 concentration of 2.0 mg/ml or 4.0 mg/ml for expression in a tube. SDS-PAGE analysis showed that the expression amount of PDGF-IM-P high-copy screening strain is significantly higher than that of the other two strains.

Figure 9:
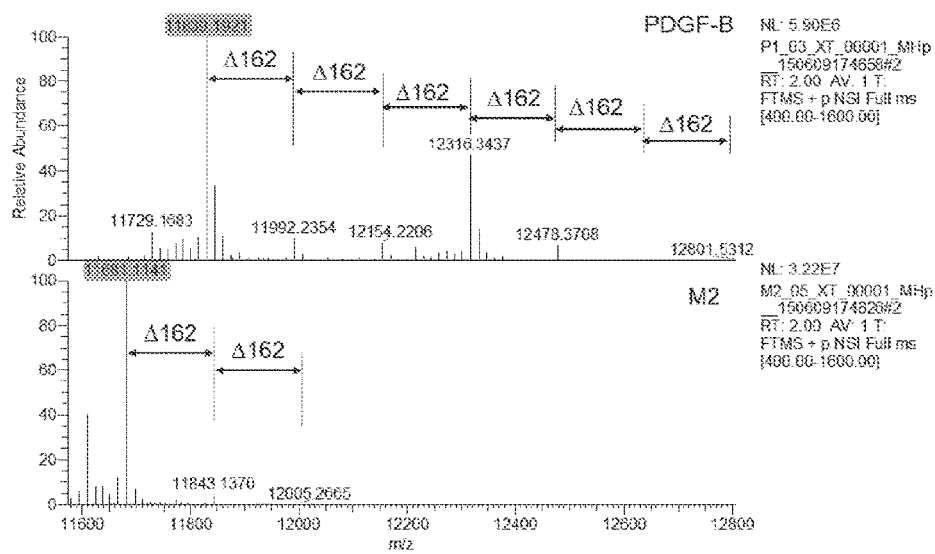

FIG. 9. LC/MS plots of PDGF-B wild-type and PDGF-M2 mutants.

DETAILED DESCRIPTION OF THE INVENTION

The embodiments of the present invention will be described in detail below in combination with the examples, however, those skilled in the art will appreciate that the following examples are merely intended to illustrate the invention and should not be construed as limiting the scope of the invention. Those without the specific conditions specified in the examples should be carried out under normal conditions or the conditions recommended by the manufacturer. The reagents or instruments without manufacturers specified are all commercially available conventional products.

Figure 2:
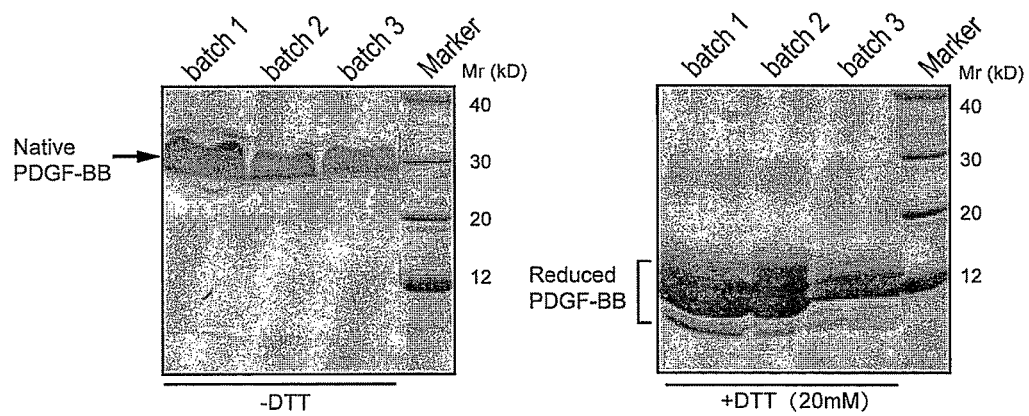

In previous studies, we have successfully employed *Pichia pastoris* expression system to express rhPDGF-BB$^{Thr6}$ with five amino acids deleted at N-terminus with a expression level of up to 100 mg/L (see CN Patent No.: ZL200410068993.2). PDGF-B$^{Thr6}$ is selected as research subject in order to ensure homogeneity of expressed protein without biological activity impaired. However, further studies demonstrate that, rhPDGF-B$^{Thr6}$ monomer expressed by *Pichia pastoris* still exhibits various forms with heterogeneous molecular weights ranging from 10 to 15 kDa (FIG. 2).

The following examples are carried out by engineering based on rhPDGF-B$^{Thr6}$, and all the descriptions of the sites or positions are based on the wild-type PDGF-B (109 amino acids).

Genbank number of the amino acid sequence of the wild-type PDGF-B is NM-002608.2.

The amino acid sequence of rhPDGF-BB$^{Thr6}$ is:

```
                                              (SEQ ID NO: 1)
TIAEPAMIAECKTRTEVFEISRRLIDRTNANFLVWPPCVEVQRCSGCCNN
RNVQCRPTQVQLRPVQVRKIEIVRKKPIFKKATVTLEDHLACKCETVAAA
RPVT.
```

The nucleic acid sequence of rhPDGF-BB$^{Thr6}$ is:

```
                                              (SEQ ID NO: 2)
5'-ACCATTGCTGAGCCGGCCATGATCGCCGAGTGCAAGACGCGCACCG

AGGTGTTCGAGATCTCCCGGCGCCTCATAGACCGCACCAACGCCAACTT

CCTGGTGTGGCCGCCCTGTGTGGAGGTGCAGCGCTGCTCCGGCTGCTGC

AACAACCGCAACGTGCAGTGCCGCCCCACCCAGGTGCAGCTGCGACCTG

TCCAGGTGAGAAAGATCGAGATTGTGCGGAAGAAGCCAATCTTTAAGAA

GGCCACGGTGACGCTGGAAGACCACCTGGCATGCAAGTGTGAGACAGTG

GCAGCTGCACGGCCTGTGACC-3'.
```

Materials and methods
Construction of recombinant expression clones
DNA sequences encoding various PDGF mutants were synthesized by Shanghai Sangon Inc.. The gene fragments were cloned into the expression vector pMEX9K (see patent ZL02117906.9) via restriction sites XhoI and EcoRI and confirmed by sequencing. The recombinant plasmids were extracted, linearized by SalI digestion, and then transformed into *Pichia pastoris* expression strain GS115 competent cells by electroporation. The yeast transformants were screened by histidine-deficient MD plates and the positive recombinant yeast strains were identified by PCR.

Induction expression of recombinant proteins
The single clones of the recombinant yeast strain were inoculated into a flask of 25 mL BMGY medium (BMGY medium is prepared as follows: 10 g yeast extract powder and 20 g tryptone were weighed, dissolved in 700 ml water, autoclaved at 121° C. for 20 min; cooled to room temperature, added 100 ml 1 M potassium phosphate buffer, 100 ml 10×YNB and 100 ml 10×GY, and stored at 4° C. Wherein: 10×YNB (13.4% yeast nitrogen source base), 10×GY (10% glycerol), 1 M potassium phosphate buffer (132 ml 1M K$_2$HPO$_4$ and 868 ml 1M KH$_2$PO$_4$ were measured, adjusted to pH 6.0 ±0.1 with phosphoric acid or KOH, autoclaved at 121° C. for 30 min and stored at room temperature.) Yeast Extract (LP0021) is a product of OXOID Inc. and Peptone (211677) is a product of B&D Inc.), cultured and propagated at 28-30° C. with 220-250 rpm to OD$_{600}$=2-6 (about 16-18 hours). 25 ml yeast culture was inoculated into a flask containing 1L BMGY, and continued to culture and propagate at 28-30° C. with 220-250 rpm to OD$_{600}$=2-6. Yeasts were collected by centrifugation at room temperature with 1500-3000 g for 5 min. The supernatant was removed and the yeasts were resuspended with 1L BMMY medium to initiate expression induction. The induction temperature was 28° C. and the rotational speed was 220 rpm. Methanol was added every 24 hours until the final concentration is 0.5%, and the induction time was 72 hours. After the induction was complete, the supernatant containing the recombinant protein was collected by centrifugation with 7000 rpm at room temperature.

Figure 5:
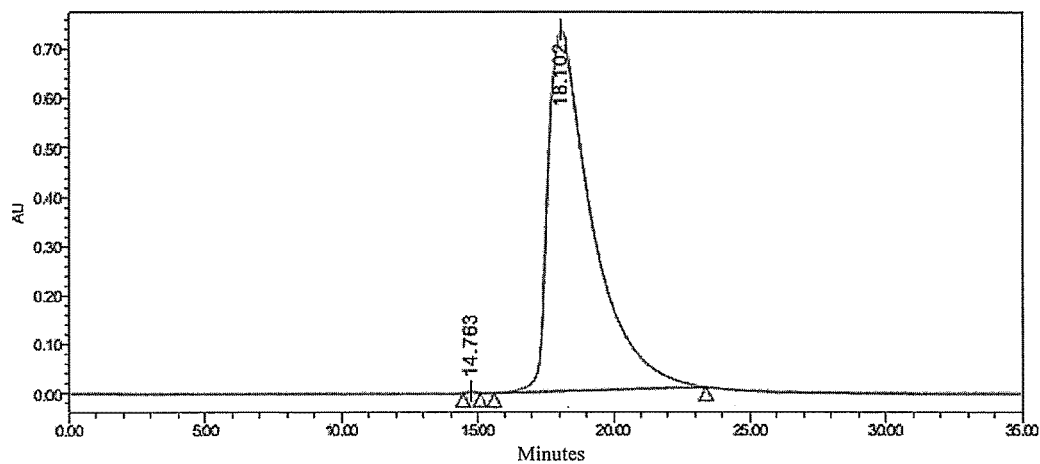

Purification of recombinant proteins
The expression supernatant of *Pichia pastoris* was adjusted into an appropriate buffer by centrifugation and filtration, and subsequently subjected to hydrophobic interaction chromatography (Phenyl Sepharose 6 Fast Flow), ion exchange chromatography (Source 30S) and gel filtration chromatography (Hiload Superdex 75 prep grade) to obtain the protein of interest with a purity >95% (FIG. 5). The chromatographic media are all products from GE Amersham Bioscience Inc..

Hydrophobic chromatography was carried out as follows. (1) Yeast expression supernatant was adjusted for conductivity with ½ volume of conditioning buffer (60 mM PB, 3M (NH$_4$)$_2$SO$_4$, pH 7.2). (2) As described in the instruction, the column was equilibrated with an equilibration buffer (20 mM PB, 1M (NH$_4$)$_2$SO$_4$, pH 7.2). (3) The sample was loaded to the column, thereafter the column was washed with the equilibration buffer until the baseline is flat. (4) The column was eluted with an elution buffer (20 mM PB, 50% ethylene glycol, pH 7.2) to collect the protein of interest.

Ion exchange chromatography was carried out as follows. (1) The Phenyl HS elution peak was diluted with an equilibration buffer (20 mM PB, pH 7.2) to a conductivity of 6 mS/cm or less. (2) According to the method in the instruction, the column was equilibrated with the equilibration buffer. (3) The sample was loaded to the column, thereafter the column was washed with the equilibration buffer until the baseline is flat. (4) The column was eluted with a gradient of elution buffer (20 mM PB, 1M NaCl, pH 7.2) to collect the protein of interest.

Gel filtration chromatography was carried out as follows. (1) The column was equilibrated with PBS buffer (20 mM PB, 0.15M NaCl, pH 7.2). (2) The Source 30S elution peak was loaded with a loop, and the volume of each loading was not more than 3% of the column volume. (3) The column was washed with PBS buffer to collect the protein of interest.

SDS-PAGE detection of recombinant proteins

30 µl purified protein with a suitable concentration was added to 10 µl 4×SDS-PAGE buffer (with and without 20 mM DTT) respectively, denatured at 100° C. for 5 min and centrifuged. Then 30 µl of the supernatant was taken for SDS-PAGE electrophoresis analysis (separation gel is 15%). Following the electrophoresis, the gel was stained with Coomassie Brilliant Blue R250.

Western blot (WB) detection of recombinant proteins

The sample was prepared in the same way as in SDS-PAGE. 3 µl sample was taken for SDS-PAGE. Following the electrophoresis, the proteins were transferred to a nitrocellulose membrane with 300 mA constant current for 1 h and blocked with 5% skim milk/TBST at room temperature for 1 h. The primary antibody PDGF-B (F-3) (Santa Cruz Biotechnology, SC-365805) was 1:1000 diluted, coated at room temperature for 1 h, and washed with TBST for several times. HRP-labeled secondary antibody (Cell Signaling Technology, #7076) was 1:10000 diluted, incubated at room temperature for 1 h, and washed with TBST. The substrate was added and imaged with an LAS400 mini gel imaging system (GE).

Sequencing of N-terminal amino acid sequence

Sample preparation and SDS-PAGE processes were the same as the above. Following the completion of the electrophoresis, the proteins were transferred to a PVDF membrane with CAPS electroblotting buffer at 300 mA constant current for 1 h, and stained with 0.1% Coomassie Brilliant Blue R250, immediately after that, fully decolored with 50% methanol until the protein bands were visible. The protein bands to be determined were cut off and sent to Chromatography Laboratory of Biomedical Analysis Center, Military Medical Academy for determination.

Detection of protein glycosylation

5 µl of the sample and the positive control IFN-ω were added into 3 µl of 10×glycoprotein denaturation buffer (containing NEB PNGase F enzyme) and 15 µl of water, and heated at 100° C. to denature for 10 min. After cooling, 3 µl NP-40, 3 µl G7 buffer (containing NEB PNGase F enzyme) and 2 µl peptide N-glycosidase F (PNGase F) (a product of New England Biotech Inc. (NEB)) were added and digested at 37° C. for 3 h. Following the completion of the digestion, the sample was heated at 100° C. to inactivate the enzyme and then subjected to SDS-PAGE electrophoresis. Following the completion of the electrophoresis, staining was performed using a glycoprotein staining kit (Themo Scientific, #24562). Firstly, the gel was added into 100 ml 50% methanol and fixed for 30 min; the gel was washed several times with 3% acetic acid, transferred to 25 ml Oxidizing Solution and shaken gently for 15 min; the gel was washed several times with 3% acetic acid, transferred to 25 ml Glycoprotein Staining Reagent and shaken gently for 15 min; thereafter, the gel was transferred to 25 ml Reducing Solution and shaken gently for 5 min; then, the gel was washed with 3% acetic acid and rinsed with deionized water.

Detection of PDGF-B biological activity

BALB/C 3T3 cells (purchased from Beijing Xiehe Cell Resource Center) were cultured in DMEM complete medium (Life Technology) containing 10% FBS under a condition of 37° C. and 5% carbon dioxide. After digestion and collection, the cells were prepared as cell suspension containing 5.0×10$^4$ cells per ml with a complete broth, inoculated into a 96-well cell culture plate (100 µl per well), and followed by culturing under a condition of 37° C. and 5% carbon dioxide. 24 hours later, the medium was exchange into a maintainance medium (DMEM containing 0.4% FBS), followed by culturing under a condition of 37° C. and 5% carbon dioxide. Upon 24 hours of culturing, the culture medium was discarded and added apre-gradient diluted PDGF-BB solution (100 µl per well). The cells were cultured for another 64 to 72 hours under the action of proteins, and were assayed for cell proliferation with WST-1 method as follows: 10 µl WST-1 solution (Roche, 11644807001) was added into each well, cultured under a condition of 37° C. and 5% carbon dioxide for 3 hours, and then measured for the absorbance at a wavelength of 450 nm using a microplate reader (reference wavelength: 630 nm). The experimental data were processed by a four-parameter regressive calculation method. The EC$_{50}$ values of the two proteins were calculated respectively. The experiment was repeated three times. The difference statistical analysis between the two groups was performed by t-test.

Figure 3:
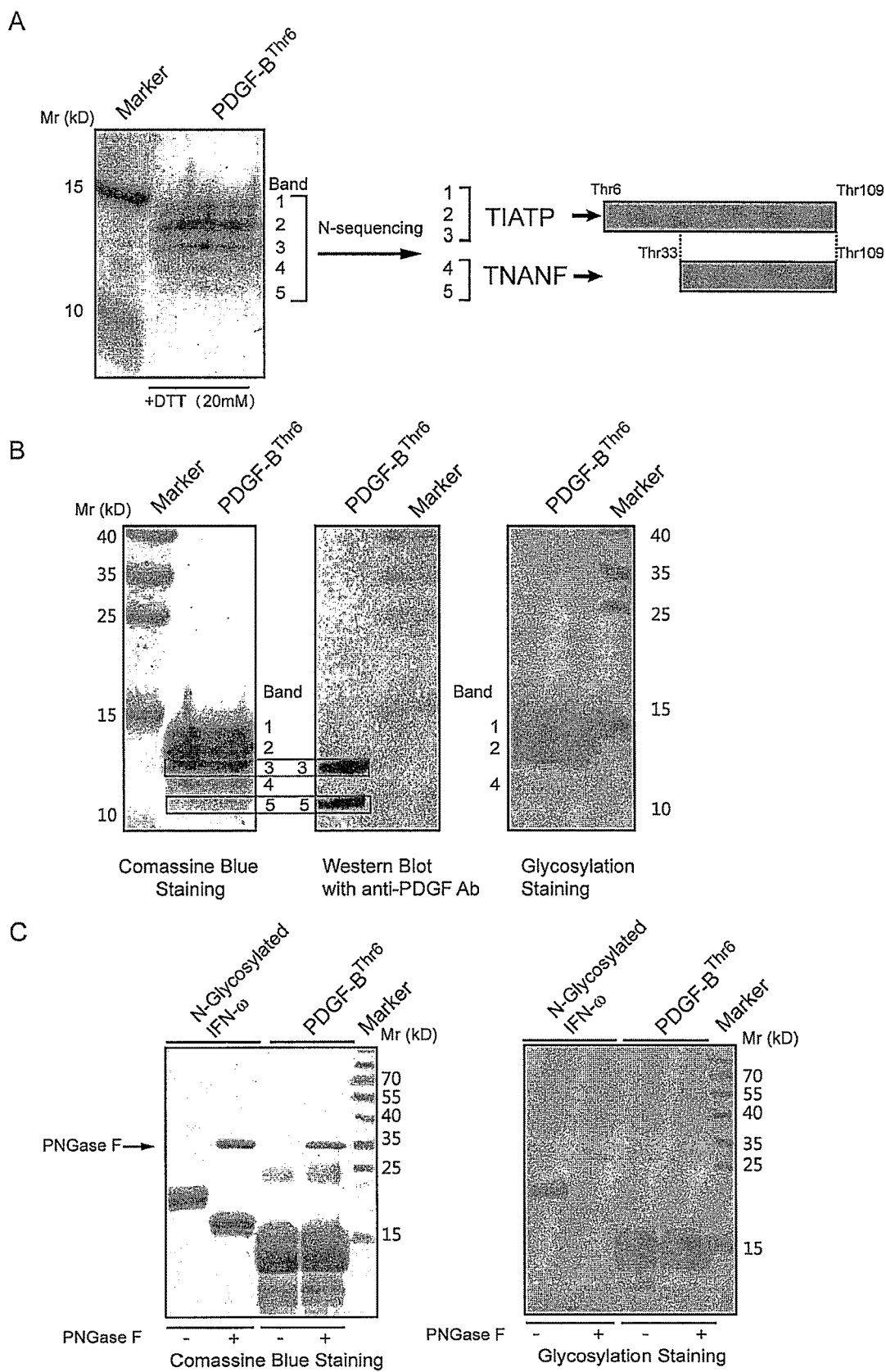

Example 1. The co-effect of the proteolysis and glycosylation contributes to the formation of diverse monomers of PDGF-BB$^{Thr6}$ The inventors firstly suspected that proteolysis is the cause of the formation of diverse PDGF-B monomers. By reducing SDS-PAGE electrophoresis, different monomers of PDGF-B were separated and five bands were detected via Coomassie Brilliant Blue staining (FIG. 3A). The five protein bands were subjected to sequencing for N-terminal amino acid sequence, and the results showed that the first five amino acid residues at N-terminus in the first, second and third bands were all TIAEP, corresponding to the correct N-terminal sequence of PDGF-B$^{Thr6}$, while the first five amino acid residues at N-terminus in the fourth and fifth bands were TNANF. The alignment of protein sequences determined that the fourth and fifth protein fragments were the truncated proteins generated by proteolytic cleavage at Arg32-Thr33 (FIG. 3A).

However, this cannot explain the reason for the formation of at least 5 kinds of PDGF monomers. The difference in molecular weights between bands 1, 2, 3 and bands 4, 5 might be due to C-terminal cleavage. To answer this question, the inventors performed WB assay using a specific monoclonal antibody (F-3) against PDGF-B C-terminus (Santa Cruz Biotechnology, SC-365805). The result showed that only two of the five bands were detected. But interestingly, the two bands bound to the antibody appeared to correspond to the third and fifth protein fragments (FIG. 3B). If the first, second, and fourth protein fragments cannot be detected by the antibodies due to the C-terminal cleavage, their molecular weights should be smaller. However, this is clearly not consistent with the result of electrophoresis assay. This means that there are other reasons to be found.

In order to analyze whether PDGF-B was glycosylated, PDGF was digested with peptide N-glycosidase F (PNGase F), and SDS-PAGE and glycoprotein staining were performed simultaneously. PNGaseF is an amidase which can act on almost all N-glycan chains in a glycopeptide/glycoprotein, cleaves between the innermost GlcNAc and asparagine residues of the sugar chain moiety, and converts asparagine into aspartic acid (10), and is the most widely used enzyme in the identification of N-glycoprotein in the glycoprotein proteomics research. The recombinant IFN-ωprotein expressed in *Pichia pastoris* acts as a positive control of N-glycosylated protein. Coomassie Brilliant Blue staining result showed that there was no change in the relative molecular weight of PDGF-B protein before and after the cleavage, indicating that PDGF-B protein did not undergo N-glycosylation (FIG. 3C, left). However, the glycoprotein staining result indicated that PDGF-B is indeed a glycoprotein (FIG. 3C, right). This means that PDGF-B secreted by *Pichia pastoris* was O-glycosylated. Meanwhile, further analysis showed that only three protein fragments were detected in the sugar staining, which should correspond to bands 1, 2 and 4 in the SDS-PAGE result respectively (FIG. 3B). This is also consistent with the result of the above WB assay: the first, second and fourth protein fragments were glycosylated at C-terminus thereof, thus affecting the binding of PDGF-B$^{Thr6}$ to the antibody.

Combining the above experimental results, the inventors deduced that the several forms of PDGF-B$^{Thr6}$ monomers resulted from the co-effect of the proteolysis and differentially post-translational glycosylation occurring between amino acids Arg32-Thr33 at positions 27/28 (Table 1).

TABLE 1

Analysis on PDGF-B$^{Thr6}$ modifications

| Band | modification type |
| --- | --- |
| 1 | complete PDGF, O-glycosylation |
| 2 | complete PDGF, O-glycosylation |
| 3 | complete PDGF |
| 4 | Arg32-Thr33 truncated, O-glycosylated |
| 5 | Arg32-Thr33 truncated |

Note:
The complete PDGF in the table refers to PDGF-B$^{Thr6}$, i.e., a PDGF-B with 5 amino acids deleted at N-terminus.

Figure 4:
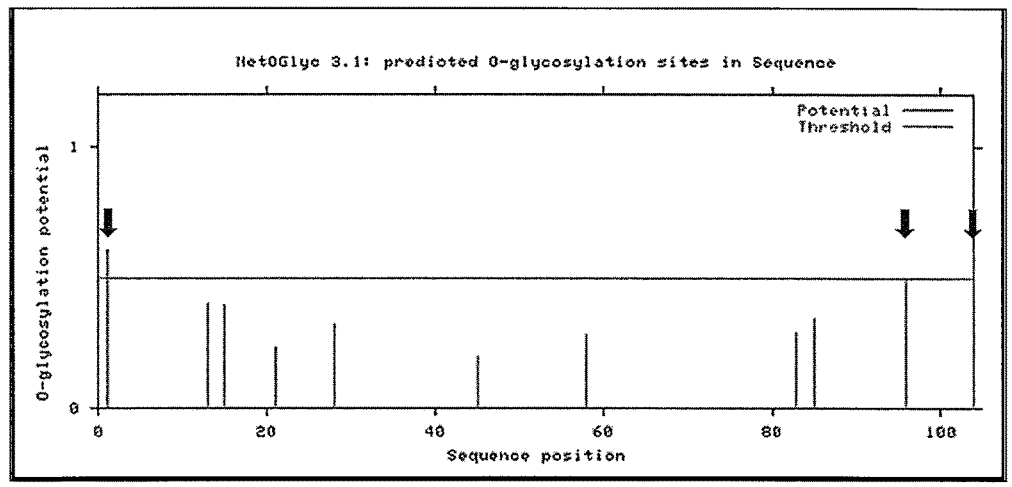

Example 2. Construction of PDGF-M1 and PDGF-M2 modifiers and Detection of Protein Properties Moreover, the inventors would like to confirm the above-mentioned deduction, and expected the expression of PDGF-B in *Pichia pastoris* to be homogenous. Firstly, the inventors would like to determine the possible O-glycosylation sites. The prediction of the glycosylation sites of PDGF-B$^{Thr6}$ protein sequence was performed using online website CBS (www.CBS.dtu.dk) (11). The result showed that Thrs at positions 6, 101 and 109 are the possible O-glycosylation modification sites (FIG. 4). Compared with N-glycosylation, there is no definite motif for O-glycosylation sites, so the prediction thereof is also relatively difficult. However, the predicted potential glycosylation sites at positions 6, 101 and 109 are consistent with our results: there should be glycosylation modifications (Thr101, Thr109) at C-terminus of the PDGF-B$^{Thr6}$ protein, since they hindered the binding to the antibody; there should be glycosylation modification site(s) before Thr33, which could explain the fact that there was only one (Band 4) glycosylation-modified variant for the digested PDGF-B, but there were two bands (Bands 1, 2) for glycosylated PDGF-B monomer without digestion (FIG. 3B; Table 1). In order to confirm the predicted results, we constructed two mutants PDGF-M1 and PDGF-M2 of PDGF-B$^{Thr6}$. Two glycosylation sites at C-terminus were mutated in PDGF-M1, and all three potential glycosylation sites were mutated in PDGF-M2 (See FIG. 6A for the pattern of mutations). Meanwhile, in order to remove the protease cleavage site Arg32-Thr33, we mutated Arg32 to Pro, considering the evolutionary selection of amino acids. We noted that the mature PDGF-B protein has 60% amino acid sequence homology with PDGF-A, and both have a high similarity in terms of structure and function, whereas the amino acid in the corresponding position of PDGF-A protein is Pro.

The amino acid sequence of PDGF-M1 is:

```
                                            (SEQ ID NO: 3)
TIAEPAMIAECKTRTEVFEISRRLIDPTNANFLVWPPCVEVQRCSGCCN
NRNVQCRPTQVQLRPVQVRKIEIVRKKPIFKKATVTLEDHLACKCEAVA
AARPVA;
```

The nucleotide sequence of PDGF-M1 is:

```
                                            (SEQ ID NO: 4)
ACCATTGCTGAGCCGGCCATGATCGCCGAGTGCAAGACGCGCACCGAGG

TGTTCGAGATCTCCCGGCGCCTCATAGACCCCACCAACGCCAACTTCCT

GGTGTGGCCGCCCTGTGTGGAGGTGCAGCGCTGCTCCGGCTGCTGCAAC

AACCGCAACGTGCAGTGCCGCCCCACCCAGGTGCAGCTGCGACCTGTCC

AGGTGAGAAAGATCGAGATTGTGCGGAAGAAGCCAATCTTTAAGAAGGC

CACGGTGACGCTGGAAGACCACCTGGCATGCAAGTGTGAGGCAGTGGCA

GCTGCACGGCCTGTGGCC.
```

The amino acid sequence of PDGF-M2 is:

```
                                            (SEQ ID NO: 5)
AIAEPAMIAECKTRTEVFEISRRLIDPTNANFLVWPPCVEVQRCSGCCN
NRNVQCRPTQVQLRPVQVRKIEIVRKKPIFKKATVTLEDHLACKCEAVA
AARPVA;
```

The nucleotide sequence of PDGF-M2 is:

```
                                            (SEQ ID NO: 6)
GCCATTGCTGAGCCGGCCATGATCGCCGAGTGCAAGACGCGCACCGAGG

TGTTCGAGATCTCCCGGCGCCTCATAGACCCCACCAACGCCAACTTCCT

GGTGTGGCCGCCCTGTGTGGAGGTGCAGCGCTGCTCCGGCTGCTGCAAC

AACCGCAACGTGCAGTGCCGCCCCACCCAGGTGCAGCTGCGACCTGTCC

AGGTGAGAAAGATCGAGATTGTGCGGAAGAAGCCAATCTTTAAGAAGGC

CACGGTGACGCTGGAAGACCACCTGGCATGCAAGTGTGAGGCAGTGGCA

GCTGCACGGCCTGTGGCC.
```

Figure 6:
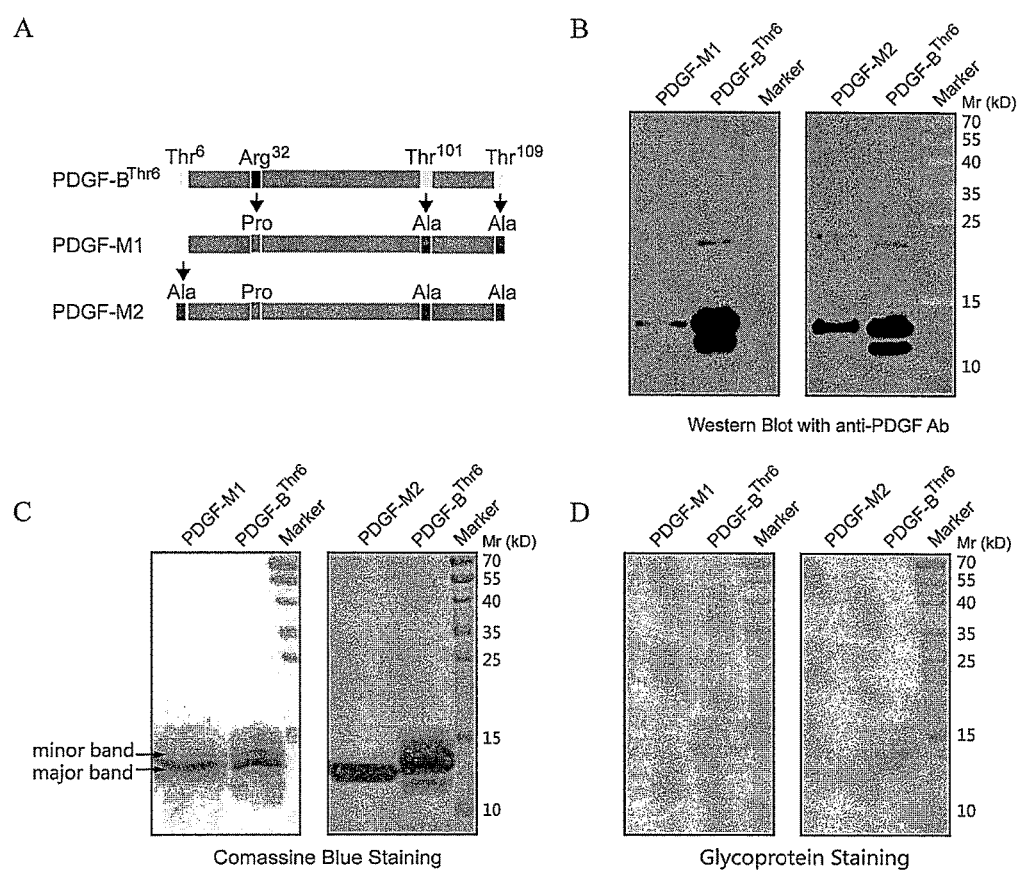

DNA sequences encoding PDGF-M1 and PDGF-M2 were inserted into expression vector pMEX9K, and integrated into the *Pichia pastoris* strain GS115. The expression was induced by methanol and proteins were purified via chromatography. The purified PDGF-B proteins were subjected to SDS-PAGE, glycoprotein staining and Western blotting detection, in order to determine the properties of the engineered protein. WB result showed that only single band could be detected after the two mutants were reduced, and the relative molecular mass is about 12 kDa, consistent with the expected one (FIG. 6B). SDS-PAGE result showed that PDGF-M2 is a single band, but PDGF-M1 still has a minor band above the major band (FIG. 6C). It is presumed that this band results from the glycosylation of Thr6. Glycoprotein staining result showed that the glycosylation levels of the two mutants were very low compared to those before mutation and hardly to be detected with glycoprotein staining (FIG. 6D). The above results indicated that mutation of R at position 32 to P removed the potential Kex2 protease cleavage site and prevented the formation of Thr33 truncated PDGF-B monomer, while the mutations of three glycosylation sites Thr6, 101 and 109 also abolishes the post-translational glycosylation modifications of the protein at different degrees, thereby rendering the expression of PDGF-B protein in *Pichia pastoris* homogenous.

Example 3. Detection of cell proliferation enhancing activity of PDGF-M2

In order to analyze whether the mutations of glycosylation sites Thr6-Ala, Thr101-Ala and Thr109-Ala and the mutation of Arg32-Pro KEX cleavage site could affect the biological activity of PDGF-BB, the inventors determine the proliferation activity of PDGF-B$^{Thr6}$ and PDGF-M2 on Balb/c 3T3 cells using WST-1 method. The results showed that EC50 of PDGF-B$^{Thr6}$ is 5.434±0.6475 ng/ml, while EC50 of PDGF-M2 is 3.492±0.4078 ng/ml. The t-test showed that the protein activity after engineering is higher than before engineering, with P value of 0.0117 (FIG. 7).

Example 4. Effect of PDGF-M2 Arg32 mutation on expression level

In order to enhance the expression level of PDGF-M2, the inventors carried out codon-optimization on PDGF-M2 (PDGF-IM-P) according to the codon preference of *Pichia pastoris* during protein expression using online tool JAVA Condon Adaptation Tool. The optimized encoding DNA sequence is as follows:
The DNA sequence encoding PDGF-IM-P:

(SEQ ID NO: 7)
5'GCTATCGCTGAACCAGCTATGATCGCTGAATGTAAGACTAGAAC

TGAAGTTTTCGAAATCTCTAGAAGATTGATCGACCCAACTAACGCTAAC

TTCTTGGTTTGGCCACCATGTGTTGAAGTTCAAAGATGTTCTGGTTGTT

GTAACAACAGAAACGTTCAATGTAGACCAACTCAAGTTCAATTGAGACC

AGTTCAAGTTAGAAAGATCGAAATCGTTAGAAAGAAGCCAATCTTCAAG

AAGGCTACTGTTACTTTGGAAGACCACTTGGCTTGTAAGTGTGAAGCTG

TTGCTGCTGCTAGACCAGTTGCT-3'.

The protein sequence thereof is same as PDGF-M2.
On the basis of codon optimization, Arg32 was mutated to Val (PDGF-IM-V, Val codon used is GTT) and Ile (PDGF-IM-I, Ile codon used is ATC), the expression level was compared with that of PDGF-M2 in order to analyze the effect of mutation of Arg32 on protein expression.

The nucleotide sequence of PDGF-IM-V is:

(SEQ ID NO: 8)
GCTATCGCTGAACCAGCTATGATCGCTGAATGTAAGACTAGAACTGAAG

TTTTCGAAATCTCTAGAAGATTGATCGACGTTACTAACGCTAACTTCTT

GGTTTGGCCACCATGTGTTGAAGTTCAAAGATGTTCTGGTTGTTGTAAC

AACAGAAACGTTCAATGTAGACCAACTCAAGTTCAATTGAGACCAGTTC

AAGTTAGAAAGATCGAAATCGTTAGAAAGAAGCCAATCTTCAAGAAGGC

TACTGTTACTTTGGAAGACCACTTGGCTTGTAAGTGTGAAGCTGTTGCT

GCTGCTAGACCAGTTGCT.

The nucleotide sequence of PDGF-IM-I is:

(SEQ ID NO: 9)
GCTATCGCTGAACCAGCTATGATCGCTGAATGTAAGACTAGAACTGAAG

TTTTCGAAATCTCTAGAAGATTGATCGACATCACTAACGCTAACTTCTT

GGTTTGGCCACCATGTGTTGAAGTTCAAAGATGTTCTGGTTGTTGTAAC

AACAGAAACGTTCAATGTAGACCAACTCAAGTTCAATTGAGACCAGTTC

AAGTTAGAAAGATCGAAATCGTTAGAAAGAAGCCAATCTTCAAGAAGGC

TACTGTTACTTTGGAAGACCACTTGGCTTGTAAGTGTGAAGCTGTTGCT

GCTGCTAGACCAGTTGCT.

The DNA sequences encoding PDGF-IM-P, PDGF-IM-V and PDGF-IM-I were ligated to the sequences such as restriction site(s), terminator(s), cloned into expression vector pMEX9K, and integrated into expression strain GS115. Following histidine-deficient MD plate screening, nine clones were randomly selected, and subjected to expression induced by methanol in a tube. The SDS-PAGE electrophoresis analysis of the culture supernatant demonstrated that the expression amount of PDGF-IM-P protein was significantly higher than other two strains (FIG. 8A).

The screening of GS115/PDGF-IM-P, GS115/PDGF-IM-V, and GS115/PDGF-IM-P clones with multiple inserts was carried out with G418. The expression of clones grown on plates with 2.0 mg/ml and 4.0 mg/ml G418 was analyzed, respectively. The result demonstrated that the average expression level of PDGF-IM-P was higher than the other two strains (FIG. 8B). This indicates that the mutation of Arg32 site would affect the secretion and expression level of PDGF in *Pichia pastoris*, and the mutation of this site to Pro is relatively favorable for expression.

Example 5 LC/MS detection of the glycosylation of PDGF-B and PDGF-M2 mutants

Method
The recombinant PDGF-B wild-type and PDGF-M2 mutants were reduced with DTT (2.5 mM) at 37° C. for 30 min, and diluted with buffer A (an aqueous solution containing 0.1% formic acid), followed by liquid chromatography and mass spectrometry (LC/MS) analysis. The proteins were separated on Easy-spray column (15 cm×75 μm ID, 3-μm C18 particles) using EASY-nLC system (Thermo Fisher Scientific), eluted with a linear gradient of buffer B (containing a solution of 0.1% formic acid in methanol;

0-90%, 20 min) at a flow rate of 300 nl/min. High resolution spectra were obtained using Q Exactive Mass Spectrometer (Thermo Fisher Scientific) under a condition of a resolution of 60,000, m/z 350-1600 and de-convoluted using Xtract software (Thermo Scientific).

Results

Analysis of the PDGF-B wild-type and PDGF-M2 mutant by high resolution LC/MS demonstrated that for wild-type PDGF, different isoforms containing up to 6 carbohydrate residues were detected, wherein the content of the isoform containing three carbohydrate residues was the highest. Meanwhile, glycosylation could hardly be detected for the PDGF-M2 (M2) mutant (as shown in FIG. 9).

Although the specific embodiments of the invention have been described in detail, those skilled in the art will appreciate that in accordance with all the teachings which have been disclosed, various modifications and substitutions may be made to those details and these changes are all within the scope of the present invention. The scope of the invention is given by the appended claims and any equivalents thereof.

REFERENCES

1. Ross, R., Glomset, J., Kariya, B., and Harker, L. (1974) *Proceedings of the National Academy of Sciences of the United States of America* 71, 1207-1210
2. Li, X., Ponten, A., Aase, K., Karlsson, L., Abramsson, A., Uutela, M., Backstrom, G, Hellstrom, M., Bostrom, H., Li, H., Soriano, P., Betsholtz, C., Heldin, C. H., Alitalo, K., Ostman, A., and Eriksson, U. (2000) *Nature cell biology* 2, 302-309
3. LaRochelle, W. J., Jeffers, M., McDonald, W. F., Chillakuru, R. A., Giese, N. A., Lokker, N. A., Sullivan, C., Boldog, F. L., Yang, M., Vernet, C., Burgess, C. E., Fernandes, E., Deegler, L. L., Rittman, B., Shimkets, J., Shimkets, R. A., Rothberg, J. M., and Lichenstein, H. S. (2001) *Nature cell biology* 3, 517-521
4. Fredriksson, L., Li, H., and Eriksson, U. (2004) *Cytokine & growth factor reviews* 15, 197-204
5. Tallquist, M., and Kazlauskas, A. (2004) *Cytokine & growth factor reviews* 15, 205-213
6. Deuel, T. F., and Huang, J. S. (1983) *Progress in hematology* 13, 201-221
7. Haniu, M., Rohde, M. F., and Kenney, W. C. (1993) *Biochemistry* 32, 2431-2437
8. Hart, C. E., Bailey, M., Curtis, D. A., Osborn, S., Raines, E., Ross, R., and Forstrom, J. W. (1990) *Biochemistry* 29, 166-172
9. Cook, A. L., Kirwin, P. M., Craig, S., Bawden, L. J., Green, D. R., Price, M. J., Richardson, S. J., Fallon, A., Drummond, A. H., Edwards, R. M., and et al. (1992) *The Biochemical journal* 281 (Pt 1), 57-65
10. Tretter, V., Altmann, F., and Marz, L. (1991) *European journal of biochemistry/ FEBS* 199, 647-652
11. Steentoft, C., Vakhrushev, S. Y, Joshi, H. J., Kong, Y, Vester☐Christensen, M. B., Schjoldager, K. T. B., Lavrsen, K., Dabelsteen, S., Pedersen, N. B., and Marcos☐Silva, L. (2013) *The EMBO journal* 32, 1478-1488
12. Macauley☐Patrick, S., Fazenda, M. L., McNeil, B., and Harvey, L. M. (2005) *Yeast* 22, 249-270
13. Guo, M., Hang, H., Zhu, T., Zhuang, Y, Chu, J., and Zhang, S. (2008) *Enzyme and Microbial Technology* 42, 340-345
14. Chen, P. H., Chen, X., and He, X. (2013) *Biochimica et biophysica acta* 1834, 2176-2186

What is claimed is:

1. A human, mature platelet-derived growth factor B (PDGF-B) mutant wherein the threonines at amino acid positions 101 and 109 are substituted with alanine, and wherein the PDGF-B mutant has PDGF-B activity.

2. The PDGF-B mutant of claim 1 further having substitution of the threonine at amino acid position 6 with alanine.

3. The PDGF-B mutant of claim 1 further having substitution of the arginine at amino acid position 32, the threonine at position 33, or both with proline, valine or isoleucine.

4. The PDGF-B mutant of claim 1 having an N-terminal deletion of 5 amino acids.

5. The PDGF-B mutant of claim 1 further having substitution of the threonine at amino acid position 6 with alanine and substitution of the arginine at amino acid position 32, the threonine at position 33, or both with proline, valine or isoleucine.

6. The PDGF-B mutant claim 1 further having substitution of the threonine at amino acid position 33 with proline.

7. The PDGF-B mutant of claim 1 further having substitution of the threonine at amino acid position 6 with alanine and substitution of the threonine at amino acid position 33 with proline.

8. A method for promoting cell division and proliferation, wound healing, skin regeneration, bone and damaged tooth regeneration, and joint repair, comprising the step of administering to a subject in need thereof an effective amount of the PDGF-B mutant of claim 1.

9. A PDGF homodimer formed by two PDGF-B mutants of claim 1.

10. A PDGF heterodimer formed by one PDGF-B mutant of claim 1 and one PDGF-A monomer.

11. A human, mature platelet-derived growth factor B (PDGF-B) mutant, comprising the sequence set forth in SEQ ID NO: 3 or SEQ ID NO: 5.

* * * * *

SEQUENCE LISTING

```
<160> NUMBER OF SEQ ID NOS: 9

<210> SEQ ID NO 1
<211> LENGTH: 104
<212> TYPE: PRT
<213> ORGANISM: Artificial Sequence
<220> FEATURE:
<223> OTHER INFORMATION: amino acid sequence of (rhPDGF-BB)Thr6

<400> SEQUENCE: 1

Thr Ile Ala Glu Pro Ala Met Ile Ala Glu Cys Lys Thr Arg Thr Glu
1               5                   10                  15

Val Phe Glu Ile Ser Arg Arg Leu Ile Asp Arg Thr Asn Ala Asn Phe
            20                  25                  30

Leu Val Trp Pro Pro Cys Val Glu Val Gln Arg Cys Ser Gly Cys Cys
        35                  40                  45

Asn Asn Arg Asn Val Gln Cys Arg Pro Thr Gln Val Gln Leu Arg Pro
    50                  55                  60

Val Gln Val Arg Lys Ile Glu Ile Val Arg Lys Lys Pro Ile Phe Lys
65                  70                  75                  80

Lys Ala Thr Val Thr Leu Glu Asp His Leu Ala Cys Lys Cys Glu Thr
                85                  90                  95

Val Ala Ala Ala Arg Pro Val Thr
            100

<210> SEQ ID NO 2
<211> LENGTH: 312
<212> TYPE: DNA
```

```
<213> ORGANISM: Artificial Sequence
<220> FEATURE:
<223> OTHER INFORMATION: nucleic acid sequence of (rhPDGF-BB)Thr6

<400> SEQUENCE: 2
accattgctg agccggccat gatcgccgag tgcaagacgc gcaccgaggt gttcgagatc    60
tcccggcgcc tcatagaccg caccaacgcc aacttcctgg tgtggccgcc ctgtgtggag   120
gtgcagcgct gctccggctg ctgcaacaac cgcaacgtgc agtgccgccc cacccaggtg   180
cagctgcgac ctgtccaggt gagaaagatc gagattgtgc ggaagaagcc aatctttaag   240
aaggccacgg tgacgctgga agaccacctg gcatgcaagt gtgagacagt ggcagctgca   300
cggcctgtga cc                                                       312

<210> SEQ ID NO 3
<211> LENGTH: 104
<212> TYPE: PRT
<213> ORGANISM: Artificial Sequence
<220> FEATURE:
<223> OTHER INFORMATION: amino acid sequence of PDGF-M1

<400> SEQUENCE: 3

Thr Ile Ala Glu Pro Ala Met Ile Ala Glu Cys Lys Thr Arg Thr Glu
1               5                   10                  15

Val Phe Glu Ile Ser Arg Arg Leu Ile Asp Pro Thr Asn Ala Asn Phe
            20                  25                  30

Leu Val Trp Pro Pro Cys Val Glu Val Gln Arg Cys Ser Gly Cys Cys
        35                  40                  45

Asn Asn Arg Asn Val Gln Cys Arg Pro Thr Gln Val Gln Leu Arg Pro
    50                  55                  60

Val Gln Val Arg Lys Ile Glu Ile Val Arg Lys Lys Pro Ile Phe Lys
65                  70                  75                  80

Lys Ala Thr Val Thr Leu Glu Asp His Leu Ala Cys Lys Cys Glu Ala
                85                  90                  95

Val Ala Ala Ala Arg Pro Val Ala
            100

<210> SEQ ID NO 4
<211> LENGTH: 312
<212> TYPE: DNA
<213> ORGANISM: Artificial Sequence
<220> FEATURE:
<223> OTHER INFORMATION: nucleotide sequence of PDGF-M1

<400> SEQUENCE: 4
accattgctg agccggccat gatcgccgag tgcaagacgc gcaccgaggt gttcgagatc    60
tcccggcgcc tcatagaccc caccaacgcc aacttcctgg tgtggccgcc ctgtgtggag   120
gtgcagcgct gctccggctg ctgcaacaac cgcaacgtgc agtgccgccc cacccaggtg   180
cagctgcgac ctgtccaggt gagaaagatc gagattgtgc ggaagaagcc aatctttaag   240
aaggccacgg tgacgctgga agaccacctg gcatgcaagt gtgaggcagt ggcagctgca   300
cggcctgtgg cc                                                       312

<210> SEQ ID NO 5
<211> LENGTH: 104
<212> TYPE: PRT
<213> ORGANISM: Artificial Sequence
<220> FEATURE:
<223> OTHER INFORMATION: amino acid sequence of PDGF-M2
```

<400> SEQUENCE: 5

```
Ala Ile Ala Glu Pro Ala Met Ile Ala Glu Cys Lys Thr Arg Thr Glu
1               5                   10                  15

Val Phe Glu Ile Ser Arg Arg Leu Ile Asp Pro Thr Asn Ala Asn Phe
            20                  25                  30

Leu Val Trp Pro Pro Cys Val Glu Val Gln Arg Cys Ser Gly Cys Cys
        35                  40                  45

Asn Asn Arg Asn Val Gln Cys Arg Pro Thr Gln Val Gln Leu Arg Pro
50                  55                  60

Val Gln Val Arg Lys Ile Glu Ile Val Arg Lys Lys Pro Ile Phe Lys
65                  70                  75                  80

Lys Ala Thr Val Thr Leu Glu Asp His Leu Ala Cys Lys Cys Glu Ala
                85                  90                  95

Val Ala Ala Ala Arg Pro Val Ala
            100
```

<210> SEQ ID NO 6
<211> LENGTH: 312
<212> TYPE: DNA
<213> ORGANISM: Artificial Sequence
<220> FEATURE:
<223> OTHER INFORMATION: nucleotide sequence of PDGF-M2

<400> SEQUENCE: 6

```
gccattgctg agccggccat gatcgccgag tgcaagacgc gcaccgaggt gttcgagatc    60
tcccggcgcc tcatagaccc caccaacgcc aacttcctgg tgtggccgcc ctgtgtggag   120
gtgcagcgct gctccggctg ctgcaacaac cgcaacgtgc agtgccgccc cacccaggtg   180
cagctgcgac ctgtccaggt gagaaagatc gagattgtgc ggaagaagcc aatctttaag   240
aaggccacgg tgacgctgga agaccacctg gcatgcaagt gtgaggcagt ggcagctgca   300
cggcctgtgg cc                                                       312
```

<210> SEQ ID NO 7
<211> LENGTH: 312
<212> TYPE: DNA
<213> ORGANISM: Artificial Sequence
<220> FEATURE:
<223> OTHER INFORMATION: DNA sequence encoding PDGF-IM-P

<400> SEQUENCE: 7

```
gctatcgctg aaccagctat gatcgctgaa tgtaagacta gaactgaagt tttcgaaatc    60
tctagaagat tgatcgaccc aactaacgct aacttcttgg tttggccacc atgtgttgaa   120
gttcaaagat gttctggttg ttgtaacaac agaaacgttc aatgtagacc aactcaagtt   180
caattgagac cagttcaagt tagaaagatc gaaatcgtta gaaagaagcc aatcttcaag   240
aaggctactg ttactttgga agaccacttg gcttgtaagt gtgaagctgt tgctgctgct   300
agaccagttg ct                                                       312
```

<210> SEQ ID NO 8
<211> LENGTH: 312
<212> TYPE: DNA
<213> ORGANISM: Artificial Sequence
<220> FEATURE:
<223> OTHER INFORMATION: nucleotide sequence of PDGF-IM-V

<400> SEQUENCE: 8

```
gctatcgctg aaccagctat gatcgctgaa tgtaagacta gaactgaagt tttcgaaatc    60
```

```
tctagaagat tgatcgacgt tactaacgct aacttcttgg tttggccacc atgtgttgaa      120
gttcaaagat gttctggttg ttgtaacaac agaaacgttc aatgtagacc aactcaagtt      180
caattgagac cagttcaagt tagaaagatc gaaatcgtta gaaagaagcc aatcttcaag      240
aaggctactg ttactttgga agaccacttg gcttgtaagt gtgaagctgt tgctgctgct      300
agaccagttg ct                                                          312

<210> SEQ ID NO 9
<211> LENGTH: 312
<212> TYPE: DNA
<213> ORGANISM: Artificial Sequence
<220> FEATURE:
<223> OTHER INFORMATION: nucleotide sequence of PDGF-IM-I

<400> SEQUENCE: 9
gctatcgctg aaccagctat gatcgctgaa tgtaagacta gaactgaagt tttcgaaatc       60
tctagaagat tgatcgacat cactaacgct aacttcttgg tttggccacc atgtgttgaa      120
gttcaaagat gttctggttg ttgtaacaac agaaacgttc aatgtagacc aactcaagtt      180
caattgagac cagttcaagt tagaaagatc gaaatcgtta gaaagaagcc aatcttcaag      240
aaggctactg ttactttgga agaccacttg gcttgtaagt gtgaagctgt tgctgctgct      300
agaccagttg ct                                                          312
```